| United States Patent [19] | [11] Patent Number: 4,978,750 |
| --- | --- |
| Wilke et al. | [45] Date of Patent: Dec. 18, 1990 |

[54] PROCESS FOR THE PRODUCTION OF HETEROPOLYSACCHARIDES HAVING IMPROVED PROPERTIES, MORE ESPECIALLY XANTHAN

[75] Inventors: Michaela Wilke, Schneverdingen; Klaus Szablikowski; Klaus Balser, both of Walsrode, all of Fed. Rep. of Germany

[73] Assignee: Wolff Walsrode AG, Walsrode, Fed. Rep. of Germany

[21] Appl. No.: 329,995

[22] Filed: Mar. 29, 1989

[30] Foreign Application Priority Data

Apr. 16, 1988 [DE] Fed. Rep. of Germany ....... 3812682

[51] Int. Cl.$^5$ ............................................. C08B 37/00
[52] U.S. Cl. .................... 536/114; 536/123; 536/124
[58] Field of Search .................. 536/114, 123, 124

[56] References Cited

U.S. PATENT DOCUMENTS

| 3,964,972 | 6/1976 | Patton | 435/104 |
| 4,070,535 | 1/1978 | Empey et al. | 536/114 |
| 4,259,477 | 3/1981 | Kang | 536/114 |
| 4,667,026 | 5/1987 | Jarry et al. | 536/114 |

FOREIGN PATENT DOCUMENTS

| 0048616 | 3/1982 | European Pat. Off. |
| 0140724 | 5/1985 | European Pat. Off. |
| 1487530 | 10/1977 | United Kingdom |
| 2052542 | 1/1981 | United Kingdom |

*Primary Examiner*—Ronald W. Griffin
*Assistant Examiner*—Everett White
*Attorney, Agent, or Firm*—Sprung Horn Kramer & Woods

[57] ABSTRACT

Cellulase-free heteropolysaccharides, more especially xanthan, are obtainable by treatment at special pH values, heat treatment, optionally cooling, neutralization and, optionally, subsequent precipitation in a high-turbulence precipitation bath.

15 Claims, No Drawings

PROCESS FOR THE PRODUCTION OF HETEROPOLYSACCHARIDES HAVING IMPROVED PROPERTIES, MORE ESPECIALLY XANTHAN

This invention relates to a process for the production of heteropolysaccharides, more especially xanthan, and to a cellulase-free xanthan having improved properties.

Heteropolysaccharides obtainable by fermentation of microorganisms are suitable for numerous applications by virtue of their favorable properties. Known heteropolysaccharides are, for example, dextran, pullulan, curdlan, scleroglucan, but especially xanthan.

Xanthan is an exocellular heteropolysaccharide obtainable by fermentation of Xanthomonas campestris or other Xanthomonas strains. Xanthan is produced on a industrial scale and is used, for example, as a viscosity regulator in foods and also in oil recovery production.

Xanthan, its production and use are described, for example, in GB-A-2,052,542, GB-PS No. 1,487,530, DE-A-2 737 989 and in Biotechnology, Vol. 2, 1985, Verlag Chemie, Weinheim, pages 616 et seq. The fermentation of a microorganism which produces xanthan for example generally gives a viscous culture solution in which accompanying substances, such as for example unused components of the nutrient solution or cells or cell residues or even secondary fermentation products, may be present in addition to the heteropolysaccharide.

A standard method for the purification of heteropolysaccharides, more especially xanthan, is described, for example, in Biotechnology, Vol. 3, edited by H. J. Rehm and G. Reed, 1983, Verlag Chemie Weinheim, pages 548 et seq. This method comprises precipitating the heteropolysaccharide by addition of isopropanol, filtering it off, separating off excess precipitant and working up the residue to a dry product. The product obtained in this way forms a light yellow, clouded solution when redissolved. In addition, its filterability through fine filters is greatly impeded. It is thus of advantage for the isolated, dry xanthan to contain as few gel particles (also known as microgel or micelle-like particles) as possible during its dissolution in water. The presence of these gel particles influences the filterability of dilute aqueous xanthan solution to a considerable extent and, in extreme cases, can lead to blockage of the filter. The product also has the disadvantage that it is accompanied by cellulases which accumulate as secondary products during the culturing of the Xanthomonas bacteria. These enzymes are not separated off during the known isolation processes. However, the presence of these cellulose-degrading enzyme systems is a disadvantage for the application envisaged.

The presence of cellulases may be regarded as unfavorable when a solution of xanthan is to be combined with a polysaccharide attached by $\beta$-glycoside bonds, for example cellulose or a cellulose derivative. The cellulases present in the xanthan solution bring about degradation of the cellulose or cellulose derivative in a relatively short time.

It is known that the cellulases present in a xanthan solution can be inhibited by the use of alkali hypochlorite, as described in GB-A-2,052,542. The treatment of solid xanthan with propylene oxide for example is also described in GB-PS No. 1,487,530.

The disadvantage of these methods is either their lack of efficiency or the low status of the end product from the food legislation standpoint. The scope of application of a product pretreated in this way is thus limited.

Although filtration before the actual precipitation step is described in DE-A-2 737 989, the method described therein uses filter aids based on kieselguhr. However, the disadvantage of this process is that the filtration step has to be carried out at relatively high temperatures of at least 112° C. Degradation of the xanthan molecule can be expected to take place at temperatures as high as these.

As mentioned above, it is customary in the standard process to introduce the culture solution with stirring into a suitable precipitation bath and then to separate off and dry the resulting, more or less coarse-fiber, yellow-colored xanthan precipitate.

The disadvantage of this process lies on the one hand in the formation of a coarse-fiber product with the danger that non-precipitated, gel-like xanthan is present within the fibers because the precipitation process was not completed. On the other hand, a relatively large quantity of the yellow dye formed as secondary product during fermentation with Xanthomonas campestris cultures is incorporated in the fibers in this process.

The object of the present invention is to provide an improved process for the working up of heteropolysaccharides, more especially xanthan, and also an improved xanthan.

The present invention relates to a process for the production of a cellulase-free heteropolysaccharide obtainable by fermentation of microorganisms, characterized in that (a) a solution containing the heteropolysaccharide is adjusted to a pH value outside the range of 5 to 9, (b) a heat treatment is then carried out at elevated temperature, (c) the solution is optionally cooled, (d) optionally neutralized and optionally, (e) the resulting product is introduced into a high-turbulence precipitation bath to precipitate the heteropolysaccharide.

The solution containing the heteropolysaccharide is subjected to filtration in a step (f), preferably before step (a) or after step (d), particularly in cases where it is intended to obtain a clearly soluble product.

A particularly preferred heteropolysaccharide is xanthan.

In one particularly preferred embodiment, the heteropolysaccharide, particularly xanthan, is adjusted to a pH value of 1 to 3, more especially 1 to 2, with an acid in step (a). Preferred acids are inorganic acids, such as hydrochloric acid and nitric acid, and also organic acids, such as pyruvic acid and acetic acid.

In one particularly preferred embodiment, the product is heated at a temperature of 40° to 120° C. and preferably at a temperature of 60° to 100° C., preferably for 10 to 120 minutes and more preferably for 45 to 90 minutes, in step (b).

The precipitation bath in step (e) preferably consists of an alcohol, more especially isopropanol.

Suitable filters for step (f) are, in particular, membrane filters. The pore diameter of these filters is preferably between 0.1 and 1.2 $\mu$m and more preferably between 0.3 and 0.8 $\mu$m. The crossflow filtration technique known, for example, from Bioengineering, Number 1, 1987, page 62 is preferably used for the filtration step, although basically the static filtration technique may also be applied.

The concentration of xanthan in the culture solution should not be too high because the higher viscosity of the solution associated with higher xanthan concentrations is a disadvantage during filtration. Xanthan concentrations of 0.1 to 3% are preferred, concentrations of 0.5 to 1.5% being particularly preferred.

The troublesome impurities present in any culture solution, for example cell residues, are partially separated off in the filtration step (f) and a distinctly clearer filtrate compared with the culture solution is obtained.

To inactivate any enzymes, particularly cellulases, present, the product is adjusted to a pH value outside the range mentioned above, subsequently heated and then preferably cooled and, optionally, neutralized with a suitable base.

According to the invention, the precipitation of the heteropolysaccharide, particularly xanthan, may take place from the prepared culture solution by generating turbulence in the precipitation medium by suitable units and then introducing the culture solution by dosed inflow.

Suitable precipitants are the known precipitants, preferably isopropanol, methanol and acetone.

The culture solution is advantageously introduced by pressure through a suitable nozzle system.

Intensive turbulence is generated in the precipitant, for example by the use of suitable mixing units which, at the same time, apply only minimal shear stressing to the material to be mixed. Particularly suitable units for generating the high turbulence required are jet mixers.

The high turbulence required is characterized in that the entire precipitation medium is subjected to intensive swirling and is characterized by completely irregular forms of movement. Adjacent flow regions are rapidly mixed with one another.

The present invention also relates to a clearly soluble cellulase-free xanthan which is obtainable by the process according to the invention and which 1. in the form of a 1% aqueous solution shows an extinction of at most 0.17, as measured at 600 nm (layer thickness 1.0 cm) using a spectrophotometer and
2. does not have any cellulase activity.

The xanthan according to the invention consists of fine fibers and is white in color. In contrast to the standard precipitation process mentioned above for xanthan, the precipitation process according to the invention involves a considerably shorter precipitation time.

The precipitated product, more especially xanthan, obtained by the process according to the invention may be separated off from the precipitation medium by standard separation techniques, for example filtration, and may be dried and made up by standard techniques.

The heteropolysaccharides obtainable in accordance with the invention, more especially the xanthan according to the invention, are distinguished by excellent clear solubility in water and by good filterability. In addition, a viscosity-stable combination with cellulose or cellulose derivatives, for example carboxymethyl cellulose, is present by virtue of the inactivation of the cellulases.

The irreversible inaction of the cellulases obtained by this method of treatment is reflected in the fact that, after storage, there is no change in viscosity in a solution of the heteropolysaccharides obtainable in accordance with the invention, more especially xanthan, and cellulose or cellulose derivatives. In the context of the present invention, cellulases are assumed to be completely inactivated when a mixture of the heteropolysaccharides obtained in accordance with the invention and cellulose or carboxymethyl cellulose in equal parts shows a change in viscosity of at most 5% after storage for 40 hours at 20° C., as measured by a standard method for the measurement of viscosity, for example using a rotational viscosimeter.

EXAMPLE 1

1 kg of an aqueous culture solution of Xanthomonas campestris (xanthan concentration 2.0%) was diluted with 1 kg distilled water. This solution was then filtered through a membrane filter (pore diameter 0.45 μm) by the crossflow filtration process. Nitric acid was added to the clear filtrate obtained and the pH adjusted to 1.5, followed by heating for 70 minutes at 85° C. After cooling at room temperature, the product was neutralized with sodium hydroxide.

For the subsequent precipitation step, 90% isopropanol was subjected to turbulence by means of a mixing unit (Ystral jet mixer). The pretreated culture solution was introduced into this precipitation bath through a suitable nozzle system.

In this precipitation step, the xanthan accumulates in the form of fine white fibers. After the culture solution has been sprayed in, the precipitation step is terminated. The xanthan precipitated is separated off by filtration, subsequently dried at 50° C. in a drying oven and then subjected to size reduction.

The almost white powder-form xanthan obtained dissolves in water to form a clear, highly viscous solution. After mixing in equal parts with carboxymethyl cellulose, there is a reduction in viscosity of at most 5% over a period of up to 40 hours. The extinction measures 0.13. The filterability of a 0.25% solution through a 1.2 μpm membrane filter under an excess pressure of 1 bar produced a filter value of 7 g.

In this filtration test, the reciprocal values of the filtrate volume are plotted against the reciprocal time values in a graph. The filter value is indicated by the ordinate section (1/t=0).

EXAMPLE 2

(Comparison Example)

1 kg of a culture solution of Xanthomonas campestris was introduced with stirring into 90% isopropanol, followed by stirring for 1 hour to complete the precipitation process. The precipitated xanthan is then separated off from the precipitation medium by filtration.

In this precipitation method, the isolated xanthan accumulates in the form of coarse, yellow-colored fibers. A solution prepared from this dry powder-form xanthan is clouded and yellow in color.

Mixing of this xanthan solution with carboxymethyl cellulose solution produces a distinct reduction in viscosity of around 32% of the starting value over a period of 40 hours 3.31 g polymer were obtained as the filter value. The extinction measures 1.40.

We claim:
1. A process for the production of cellulase-free heteropolysaccharides, comprising
   (a) adjusting a solution containing a heteropolysaccharide to a pH valve in the range of 1 to 3,
   (b) subsequently carrying out a heat treatment at an elevated temperature and
   (c) introducing the resultant product into a turbulent precipitation bath.

2. A process as claimed in claim 1, wherein the solution containing the heteropolysaccharide is subjected to a filtration which comes before step (a).

3. A process as claimed in claim 1, characterized in that the heteropolysaccharide is xanthan.

4. A process as claimed in claim 1, characterized in that, in step (b), the temperature is set at 40° to 120° C. for 10 to 120 minutes.

5. A process as claimed in claim 1, wherein the precipitation bath in step (c) consists essentially of alcohol.

6. A process as claimed in claim 5, wherein the alcohol is isopropanol.

7. A process as claimed in claim 1, characterized in that turbulence is generated in the precipitation bath by means of a mixing unit.

8. A process as claimed in claim 1, which further comprises cooling the solution after step (b) and before step (c).

9. A process as claimed in claim 1, which further comprises neutralizing the solution after step (b) and before step (c).

10. A process as claimed in claim 9, which further comprises subjecting the solution containing the heteropolysaccharide to a filtration after said neutralizing.

11. A process as claimed in claim 1, further comprising cooling the solution after step (b) and then neutralizing the solution prior to step (c).

12. A process according to claim 1, wherein the pH valve is in the range of 1 to 2.

13. A clearly soluble, cellulase-free xanthan which, in the form of a 1% aqueous solution, has an extraction of at most 0.17, as measured at 600 nm (layer thickness 1 cm) and which contains no active cellulases.

14. In a product containing cellulose or cellulose derivatives, wherein the improvement comprises said product containing as an additive a xanthan as claimed in claim 13.

15. A xanthan according to claim 13, produced by the process of claim 1.

* * * * *

UNITED STATES PATENT AND TRADEMARK OFFICE
CERTIFICATE OF CORRECTION

PATENT NO. : 4,978,750

DATED : December 18, 1990

INVENTOR(S) : Wilke et al.

It is certified that error appears in the above-identified patent and that said Letters Patent is hereby corrected as shown below:

Col. 6, line 13  Delete " extraction " and substitute -- extinction --

Signed and Sealed this

Twenty-fourth Day of November, 1992

Attest:

DOUGLAS B. COMER

*Attesting Officer*  *Acting Commissioner of Patents and Trademarks*